United States Patent [19]
Rheinberger et al.

[11] Patent Number: 5,889,132
[45] Date of Patent: Mar. 30, 1999

[54] DENTAL MATERIAL

[75] Inventors: Volker Rheinberger, Vaduz; Norbert Moszner, Eschen; Ulrich Salz, Lindau; Herbert Wolter, Gerchsheim; Werner Storch; Helma Baeuerlein, both of Wuerzburg, all of Liechtenstein

[73] Assignee: Ivoclar AG, Liechtenstein

[21] Appl. No.: 850,161

[22] Filed: May 2, 1997

[30] Foreign Application Priority Data

May 2, 1996 [DE] Germany .................. 196 19 046.0

[51] Int. Cl.⁶ .................................................. C08F 230/08
[52] U.S. Cl. .......................... 526/279; 556/428; 556/436; 556/437; 556/443; 556/444
[58] Field of Search ............ 526/279; 556/428, 556/436, 437, 443, 444

[56] References Cited

U.S. PATENT DOCUMENTS

| | | | |
|---|---|---|---|
| 3,375,236 | 3/1968 | Van der Castle et al. | 526/279 |
| 3,838,115 | 9/1974 | Bond | 526/279 |
| 4,359,565 | 11/1982 | Puppe et al. | |
| 4,368,314 | 1/1983 | Endo et al. | |
| 4,579,904 | 4/1986 | Orlowski et al. | 524/554 |
| 4,599,155 | 7/1986 | Suzuki et al. | |
| 4,673,354 | 6/1987 | Culler. | |

FOREIGN PATENT DOCUMENTS

| | | |
|---|---|---|
| 27 58 415 A1 | 7/1979 | Germany . |
| 44 16 857 C1 | 6/1995 | Germany . |
| 41 33 494 C2 | 3/1996 | Germany . |
| 6-93236 | 4/1994 | Japan . |
| 6093236 | 4/1994 | Japan . |
| WO 92/16183 | 10/1992 | WIPO . |
| WO 93/07230 | 4/1993 | WIPO . |

*Primary Examiner*—Bernard Lipman
*Attorney, Agent, or Firm*—Nixon, Hargrave, Devans & Doyle LLP

[57] ABSTRACT

A dental material is described which is characterized by a content of silicic acid condensates of norbornene or mercapto silanes, and which, after thiol-ene polymerisation with suitable reactants, shows only slight polymerisation shrinkage and produces polymerisates with high mechanical strength.

20 Claims, No Drawings

DENTAL MATERIAL

The invention relates to a dental material and, in particular to a dental material comprising a silicic acid condensate of a hydrolysable and polymerisable norbornene silane or a silicic acid condensate of a hydrolysable and polymerisable mercaptosilane together with a reactant for a thiol-ene polymerisation.

Hydrolysable and organically modified silanes are known and are used widely in the manufacture of scratch-resistant coatings for various-substrates and in the manufacture of fillers, adhesives and sealants or moulded articles. These silanes are either used on their own, in mixtures or in the presence of further hydrolysable and/or condensable components. The obtained hydrolysates or condensates are cured by thermal, photochemical or redox-induced means.

For example, DE-C-34 07 087 describes scratch-resistant coatings which are formed by the hydrolytic condensation of a mixture of hydrolysable titanium or zirconium compounds with a hydrolysable silane $R'_m(R''Y)_nSiX_{(4-m-n)}$, wherein R' is for example alkyl or alkenyl, R" is for example alkylene or alkenylene and X is a hydrolysable group.

Known from DE-A-35 36 716 are adhesives and sealants which were obtained by the hydrolytic condensation of one or more organosilanes with optionally further hydrolysable silanes.

Moreover, silanes with reactive double bonds are known and available on the market, such as (meth)acryloyloxy silanes of the following formula

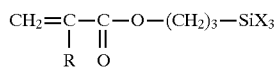

wherein R is hydrogen or methyl and X is for example halogen or alkoxy. These silanes are hydrolysable and polymerisable and can be used for the manufacture of coatings as well as adhesives and sealants. Due to the presence of only one reactive C=C double bond, these silanes, upon polymerisation, form only chain polymers or are no longer polymerisable by reaction at the C=C double bond after functionalisation. Also, as a rule there is only a short chain between the double bond and the silicon capable of forming an inorganic network so that the mechanical properties, such as for example flexibility, can only be varied within narrow limits via the organic groups.

It is known from C. J. Brinker, G. W. Scherer, "Sol-Gel-Science", Academic Press, Boston, 1990, pages 864 et seq. that through hydrolysis and condensation of vinyl- or (meth) acrylic group-containing silanes or other metal alkoxides, the "in situ" formation of fillers is possible. However, the polymerisation reactions for constructing the polymer matrix, which take place when these materials are cured, are accompanied to a greater or lesser extent by a volume shrinkage. This has a disadvantageous effect on the dimensional stability and the mechanical properties of corresponding moulded articles. The adhesion of corresponding adhesives and the strength of adhesive bonds produced therewith are likewise impaired by this polymerisation shrinkage.

Further examples of composite materials with "in situ"-formed filler particles are known from DE-A-41 33 621. To produce these materials, sols of for example metal oxides, such as titanium dioxide and zirconium dioxide, are stabilised and then condensed or polymerised into a polymer matrix. Various monomers and in particular those with (meth)acryloyloxy groups can be used to form the polymer matrix.

Several low-shrinkage matrix systems have also already been proposed. They are produced, for example, using the double ring-opening polymerisation of various cyclic monomers, such as for example spiroortho esters or carbonates (cf. US-A-4 387 215 and R. F. Brady in J. Macromol. Sci.-Rev. Macromol. Chem. Phys. C32, (1992) 135), using so-called "low profile additives" (LPA) (cf. V. A. Pattinson et al. in J. Appl. Polym. Sci. 18, (1974) 2763 and D.-S. Lee et al. in Polym. Eng. Sci. 27, (1987) 964) or using high-molecular-weight monomers, so-called macromers (cf. P. F. Rempp et al. in Adv. Polym. Sci. 58, (1984) 1). However, none of these possibilities has achieved practical significance since the synthesis of cyclic monomers is difficult and expensive, the use of LPA is limited to only a few cases, such as for example the thermal curing of unsaturated polyester resins and finally, macromers are not only expensive but, because of their high viscosity, can be provided with fillers only to a small degree.

A relatively low polymerisation shrinkage sometimes also occurs during the polyaddition of thiols to C—C unsaturated compounds, which is known from US-A-2 347 182. In this special type of polymerisation, which is also called ene-thiol or thiol-ene polymerisation, linear or crosslinked polysulphides with monosulphur form in the main chain. However, the obtained polysulphides have glass transition temperatures which are generally below or in the region of room temperature (cf. A. F. Jacobine et al. "Radiation curing of polymeric material", Editor: C. E. Hoyle et al., ACS-Symp. Ser. 417, (1990) 160 and cited there A. F. Jacobine et al. in J. Appl. Polym. Sci. 45, (1992) 471). Consequently, only soft materials with elastic or viscoelastic properties can be obtained with the conventional thiol-ene polymerisation systems.

It is the object of the invention to make available a dental material which can be polymerised, in particular using thiol-ene polymerisation, to give composite materials having high mechanical strength and hardness, with the occurrence of only a small polymerisation shrinkage.

This object is achieved by dental material according to claims 1 to 15.

The invention further relates to the use of the material as a dental adhesive or cement or dental filling material according to claims 16 to 17.

The dental material according to the invention comprises
(a) at least one silicic acid condensate of a hydrolysable and polymerisable norbornene silane of general formula (Ia)

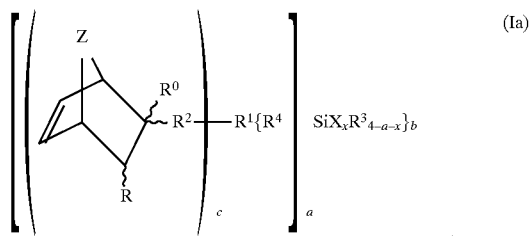

wherein the variables $R^0$, $R$, $R^1$, $R^2$, $R^3$, $R^4$, $R^5$, $R^6$, X, Y, Z, a, b, c, x have, unless stated otherwise, independently of one another, the following meanings:

$R^0 = C_1$ to $C_8$ alkyl or H;

$R = C_1$ to $C_8$ alkyl or alkenyl or $C_6$ to $C_{10}$ aryl, where these radicals can be interrupted by O or S atoms or by —O—CO—, —CO—O— or NH groups or can contain these atoms or groups in terminal position, or H or $R^2$—$R^1$—$R^4$—$SiX_xR^3_{3-x}$;

$R^1$ = missing or $C_1$ to $C_8$ alkylene or $C_6$ to $C_{14}$ arylene, arylenalkylene or alkylenarylene, where these radicals can be interrupted by O or S atoms or by —O—CO—, —CO—O— or NH groups or can contain these atoms or groups in terminal position;

$R^2$=missing or $C_1$ to $C_8$ alkylene or $C_6$ to $C_{14}$ arylene, arylenalkylene or alkylenarylene, where these radicals can be interrupted by O or S atoms or by —O—CO—,—CO—O— or NH groups or can contain these atoms or groups in terminal position;

$R^3$=$C_1$ to $C_{10}$ alkyl or alkenyl or $C_6$ to $C_{10}$ aryl, where these radicals can be interrupted by O or S atoms or can contain these atoms in terminal position;

$R^4$=—(CHR$^6$—CHR$^6$)n—, with n=0 or 1, —CHR$^6$—CHR$^6$—S—R$^5$—, —CO—S—R$^5$—, —CHR$^6$—CHR$^6$—NR$^6$—R$^5$—, —S—R$^5$, —Y—CO—NH—R$^5$— or —CO—O—R$^5$—;

$R^5$=$C_1$ to $C_8$ alkylene or $C_6$ to $C_{10}$ arylene, where these radicals can be interrupted by O or S atoms or by —O—CO—, —CO—O— or NH groups or can contain these atoms or groups in terminal position;

$R^6$=H, $C_1$ to $C_{10}$ alkyl or $C_6$ to $C_{10}$ aryl;

x=a hydrolysable group, in particular halogen, OH or alkoxy;

y=O, S or NR$^6$;

z=O or CHR$^6$;

a=1, 2 or 3;

b=1, 2 or 3;

c=1 to 6; and x=1, 2 or 3;

and with the proviso that a and/or b=1 and a+x=2, 3 or 4.

or (b) at least one silicic acid condensate of a hydrolysable and polymerisable mercaptosilane of general formula (Ib)

$[(HS—R^7)_fR^8]_gSiX_hR^9{}_{4-g-h}$ (Ib)

wherein the variables $R^7$, $R^8$, $R^9$, X, f, g and h have, unless stated otherwise, independently of one another, the following meanings:

$R^7$=$C_1$ to $C_{10}$ alkylene or alkenylene or $C_6$ to $C_{14}$ arylene or alkylarylene, where these radicals can be interrupted by O or S atoms or by —CO—O— or —O—CO— groups or can contain these atoms or groups in terminal position;

$R^8$=$C_1$ to $C_{10}$ alkylene or alkenylene or $C_6$ to $C_{14}$ arylene or alkylarylene, where these radicals can be interrupted by O or S atoms or —CO—O— or —O—CO— groups or can contain these atoms or groups in terminal position;

$R^9$=$C_1$–$C_{10}$ alkyl or alkenyl or $C_6$–$C_{14}$ aryl or alkylaryl, where these radicals can be interrupted by O or S atoms or —CO—O— or —O—CO— groups or can contain these atoms or groups in terminal position;

x=a hydrolysable group, in particular halogen, hydroxy or alkoxy;

g=1, 2 or 3;

f=1, 2, 3 or 4; and h=1, 2 or 3.

The above formulae only cover those compounds which are in agreement with the valency theory.

The norbornene silane (Ia) used according to the invention usually exists in the form of stereoisomeric mixtures, in particular as a racemate.

The possible alkyl, alkenyl and alkylene groups present in the radicals can be linear, branched or cyclic. Thus, a norbornanediyl group is e.g. a possible $C_7$ alkylene group.

Furthermore, for a, b, c or x≧1 and for f, g or h≧1, the individual groups X and the individual R groups can in each case be selected independently of one another.

There are also preferred definitions for the aforementioned variables of formulae (Ia) and (Ib) which, unless stated otherwise, can be selected independently of one another and are as follows:

For formula (Ia):

R=$C_1$ to $C_5$ alkyl or H;

R=H or $C_1$ to $C_5$ alkyl;

$R^1$=$C_1$ to $C_8$ alkylene, where these radicals can be interrupted by O or S atoms or by —O—CO— or —CO—O— groups or can contain these atoms or groups in terminal position;

$R^2$=$C_1$ to $C_8$ alkylene, where these radicals can be interrupted by O or S atoms or can contain these atoms in terminal position;

$R^3$=$CH_3$, $C_2H_5$ or phenyl;

$R^4$=—(CHR$^6$—CHR$^6$)$_n$—, —S—R$^5$—, —Y—CO—NH—R$^5$— or —CO—O—R$^5$13 ;

$R^5$=$C_1$ to $C_8$ alkylene, where these radicals can be interrupted by O or S atoms or by —O—CO— or —CO—O— groups or can contain these atoms or groups in terminal position;

$R^6$=H or $C_1$ to $C_5$ alkyl;

x=$OCH_3$ or $OC_2H_5$;

y=O or S;

z=$CH_2$;

a=1;

b=1;

c=1 or 2;

x2 or 3; and/or a+x=3 or 4.

For formula (Ib):

$R^7$=$C_1$ to $C_{10}$ alkylene or $C_6$ to $C_{14}$ arylene, where these radicals can be interrupted by O or S atoms or by —CO—O— or —O—CO— groups or can contain these atoms or groups in terminal position;

$R^8$=$C_1$ to $C_{10}$ alkylene or $C_6$ to $C_{14}$ arylene, where these radicals can be interrupted by O or S atoms or by —CO—O— or —O—CO— groups or can contain these atoms or groups in terminal position;

$R^9$=$C_1$ to $C_{10}$ alkyl;

X=$OCH_3$, $OC_2H_5$ or Cl; and/or h=2 or 3.

Preferred embodiments of the norbornene silanes used according to the invention have the following general formulae (IIa), (IIIa), (IVa) and (Va), i.e. formulae in which the indices a and/or b and/or c of general formula (Ia) have a value of 1.

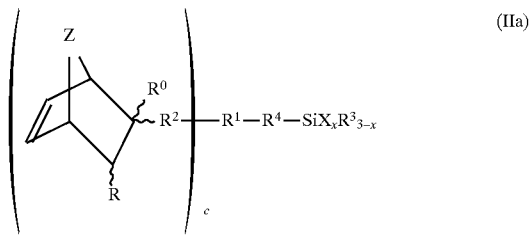
(IIa)

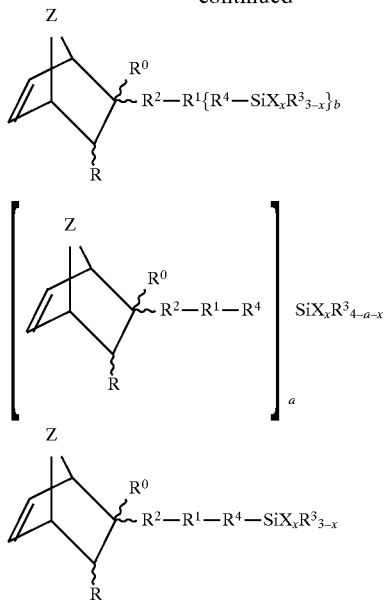  (IIIa)

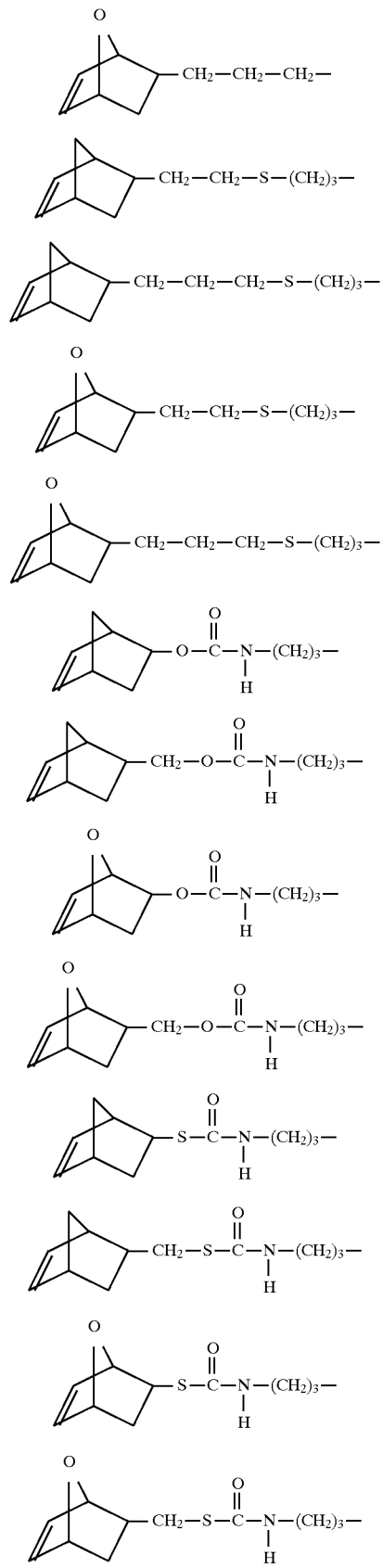

(IVa)

(Va)

The same applies to the mercaptosilanes (Ib) used according to the invention, and preferred embodiments for these mercaptosilanes are therefore represented by the following general formulae (IIb), (IIIb) and (IVb) in which the indices f and/or g have a value of 1.

$(HS-R^7)_f-R^8-SiX_hR^9_{3-h}$   (IIb)

$HS-R^7-R^8-SiX_hR^9_{3-h}$   (IIIb)

$[HS-R^7-R^8]_g SiX_h R^9_{4-g-h}$   (IVb)

Preferred examples of radicals with the index a of the norbornene silanes are given below. These examples also apply, provided the definition of the mercaptosilanes permits, to the radicals with the index g of the mercaptosilanes, by replacing the group

in each of the listed radicals of norbornene silanes by a HS group.

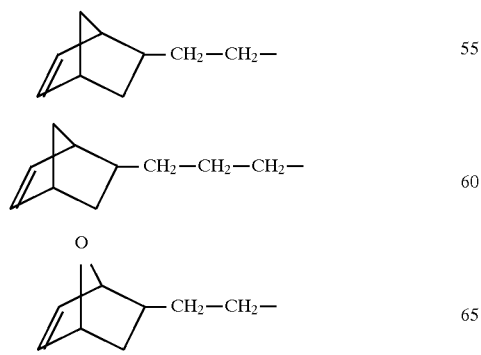

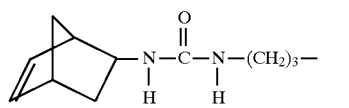
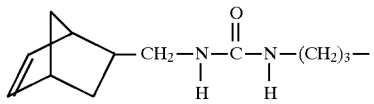
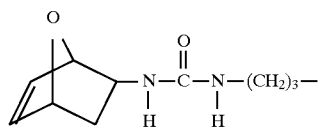
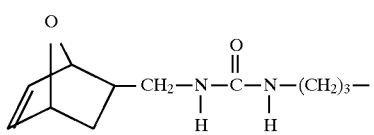
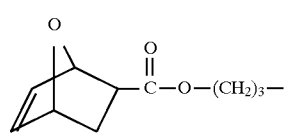
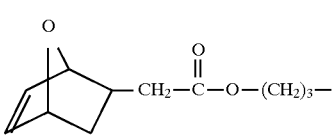
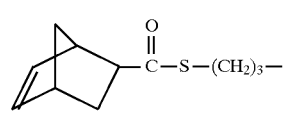
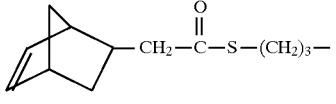
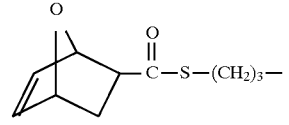
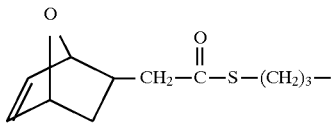
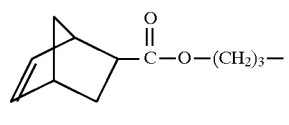
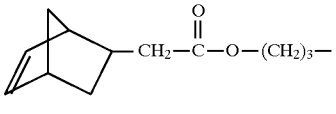
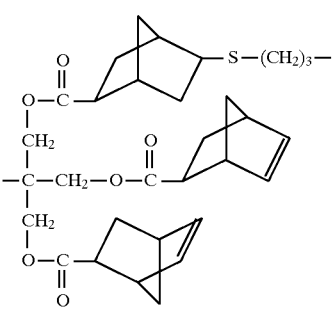
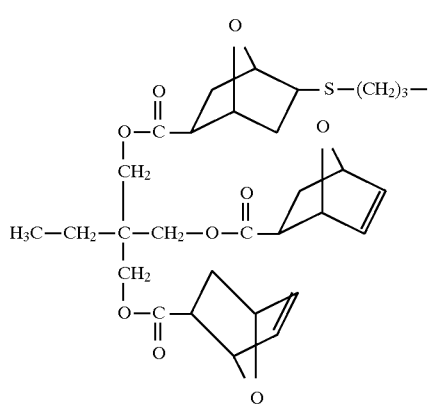
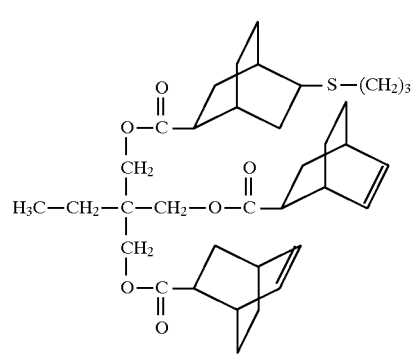
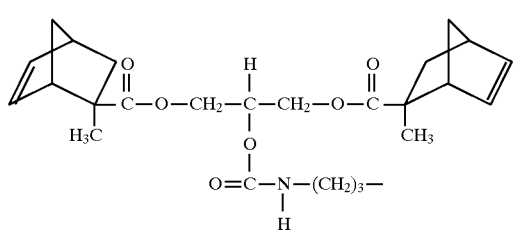
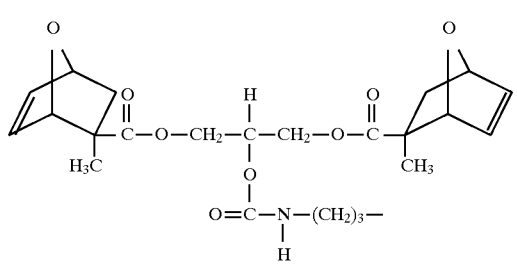

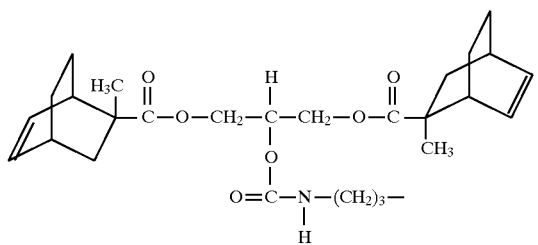
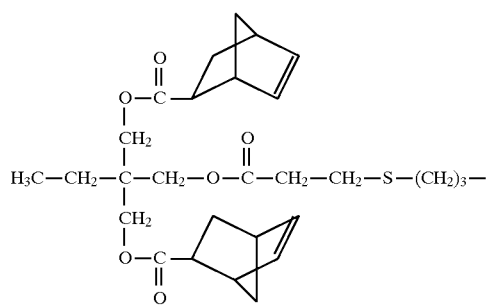
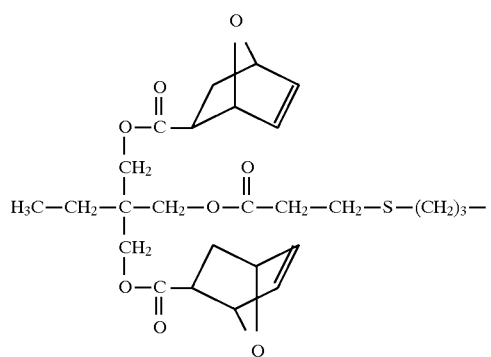
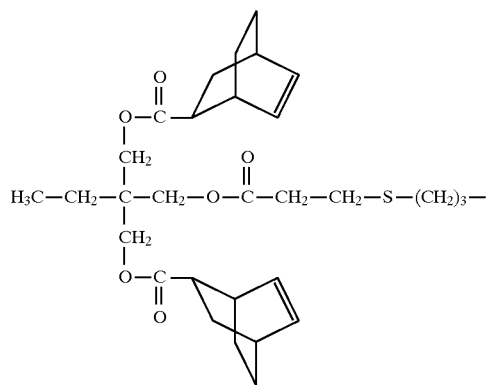
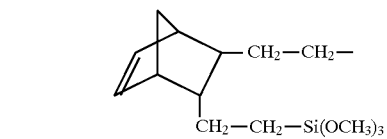
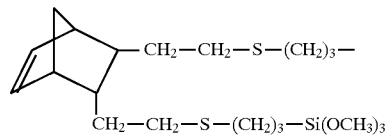
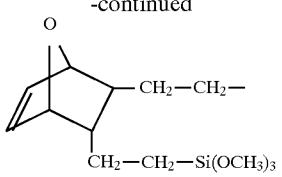
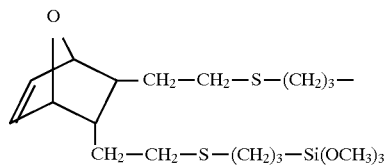
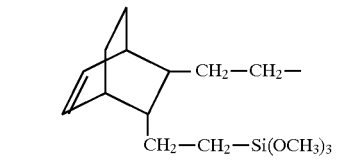
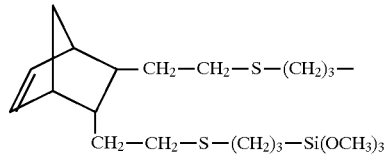
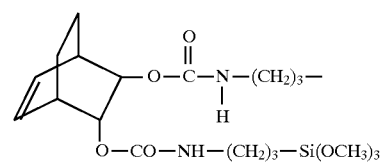
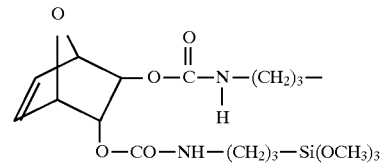
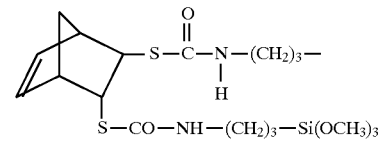
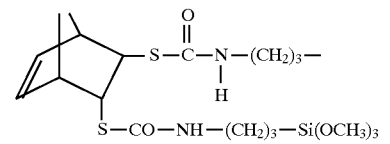
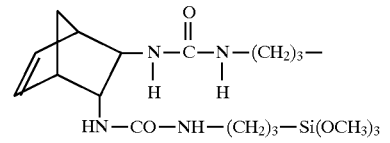
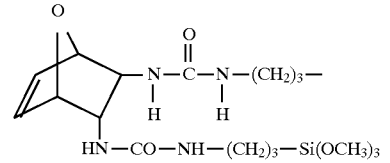

Particularly preferred mercaptosilanes (Ib) are given below:

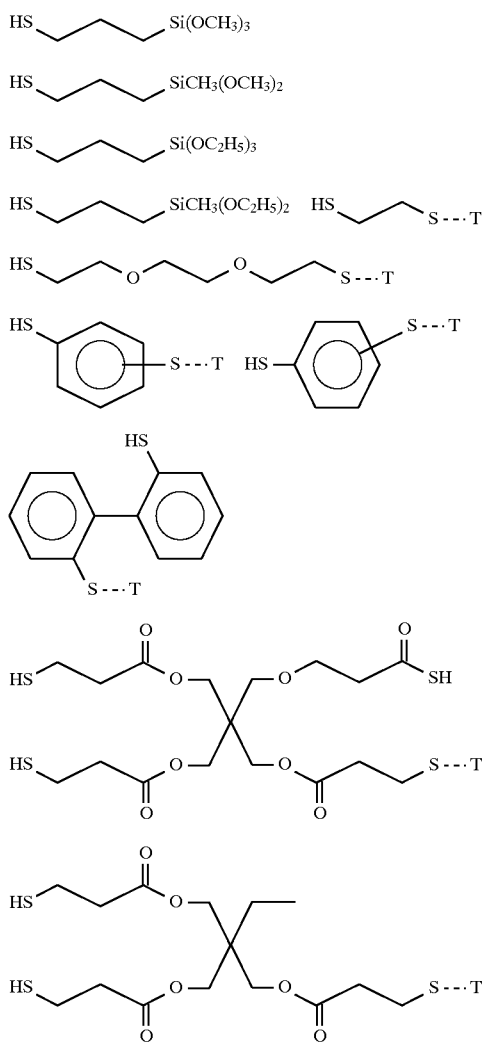

in which T is:

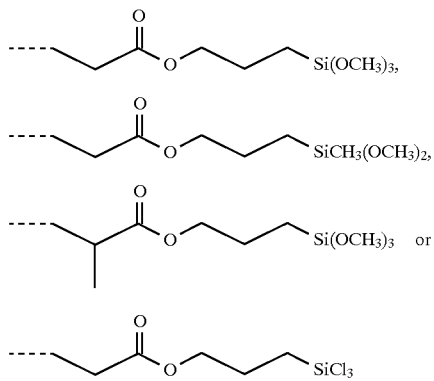

The preparation of the norbornene silanes (Ia) used according to the invention is possible using a large number of conventional addition and condensation reactions which are carried out according to the usual methods for these types of reaction.

In a first variant, norbornenes or oxabicycloheptenes, which have terminal, olefinic C=C double bonds, are subjected to hydrosilylation, a thiol or an amine addition.

The general reaction schemes are as follows, wherein the groups and indices are as defined for general formula (Ia). Simple concrete examples are also given by way of illustration.

Hydrosilylation:

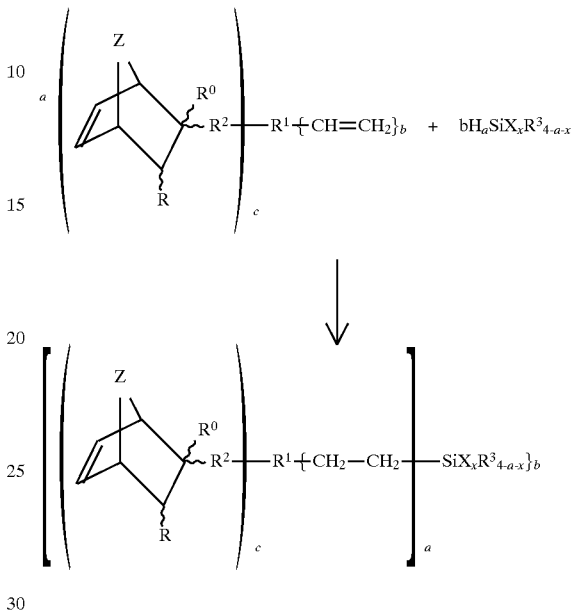

Concrete example:

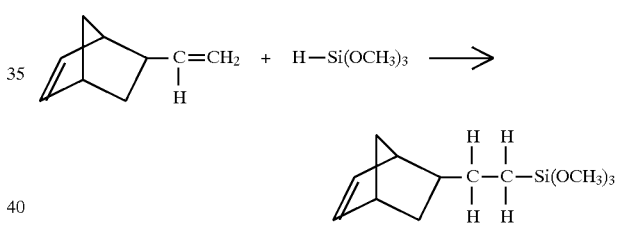

Thiol addition:

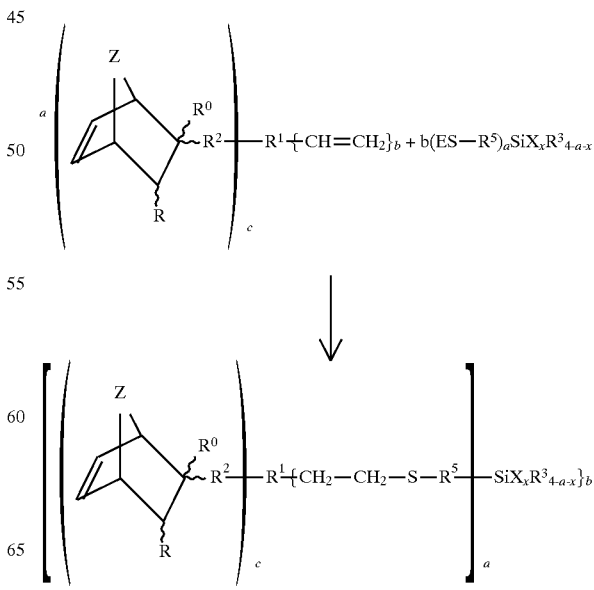

Concrete example:

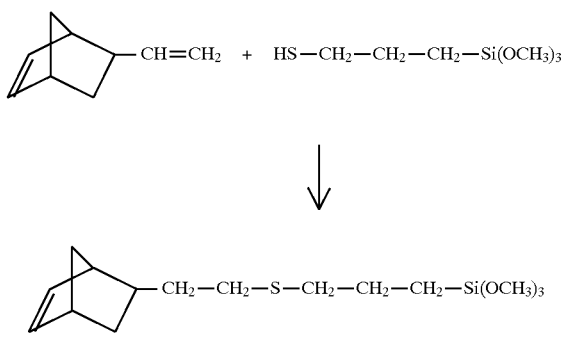

Amine addition:

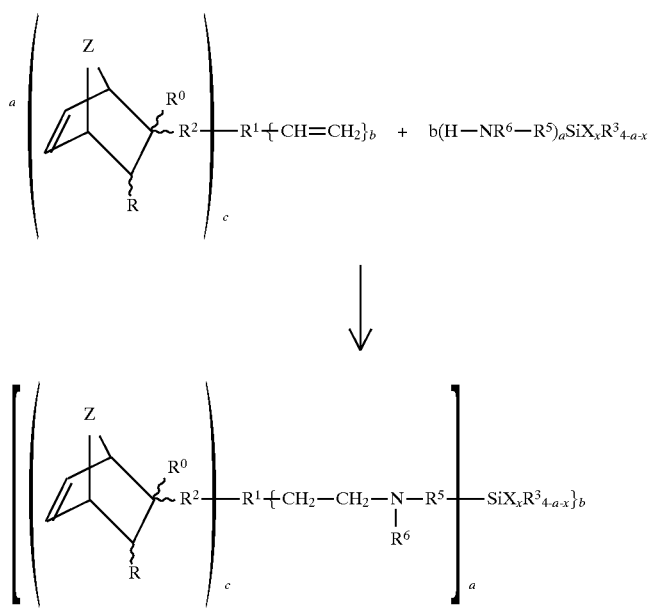

Concrete example:

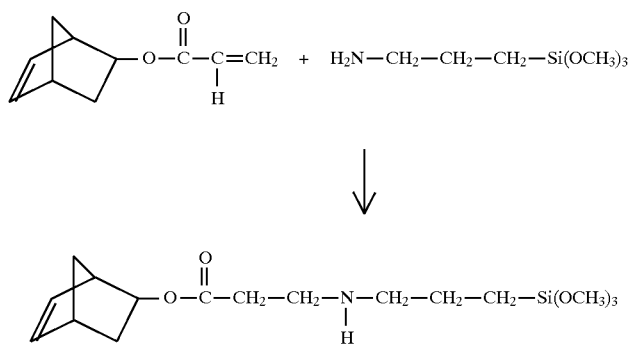

bornenes and oxabicycloheptenes of general formula XV are also reacted.

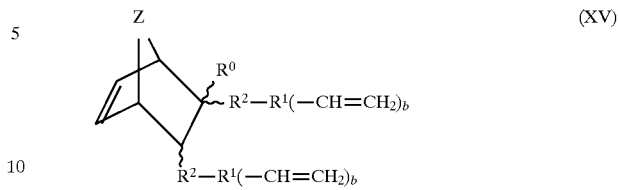

Furthermore, hydrosilylation, thiol or amine addition is also possible at the C=C double bonds of norbornenes and oxabicycloheptenes if $R^1$ has at least 2 bicyclic groups.

The radicals $R^1$ can contain up to b terminal C=C double bonds, so that in each case up to b silane units can be added to the radical $R^1$. The silanes used can contain up to a hydrogen atoms, thiol or amino groups, so that in each case up to a bicyclic groups can be added to a silane. In addition, the radicals $R^1$ can in each case contain up to c norbornene or oxabicycloheptene units. Entirely by analogy, nor- In a further process variant, bicyclic compounds, which contain hydroxyl, thiol or amino groups, are added to silanes which have isocyanate functions. The general reaction schemes are as follows, wherein the radicals and indices are as defined for general formula (Ia). Simple concrete examples are also given by way of illustration.

Isocyanate addition:

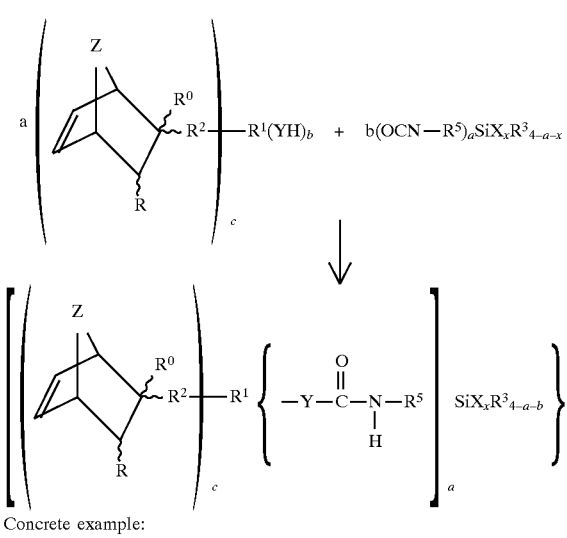

Concrete example:

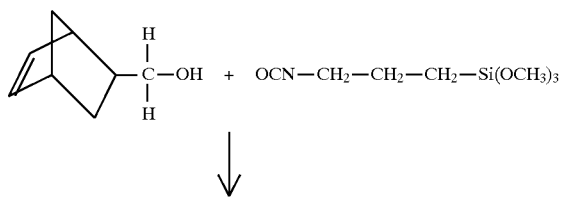

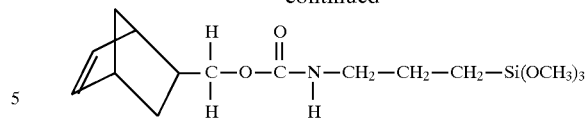

The radicals $R^1$ in the bicyclic components can in each case contain up to b hydroxyl, thiol or amino groups, so that in each case up to b silane units can be added to the radical $R^1$. The silanes used can in each case have up to a isocyanate groups, so that up to a bicyclic groups can be added to a silane. In addition, the radical $R^1$ can contain up to c norbornene or oxabicycloheptene units. Entirely by analogy, norbornenes and oxabicycloheptenes of general formula (XVI) are also reacted.

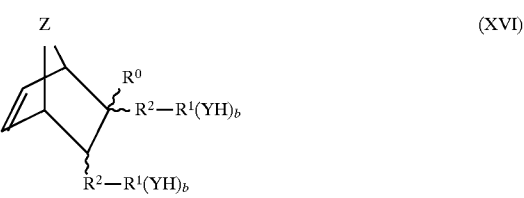 (XVI)

In further process variants, bicyclic carboxylic acid derivatives are reacted with thiol or hydroxyl group-containing silanes. The general reaction schemes are given below, wherein —A is —OH, —Cl, —H or —O—alkyl and the other groups and indices are as defined for general formula (Ia). Again, simple concrete examples are also given by way of illustration.

Reaction with silanes with thiol groups:

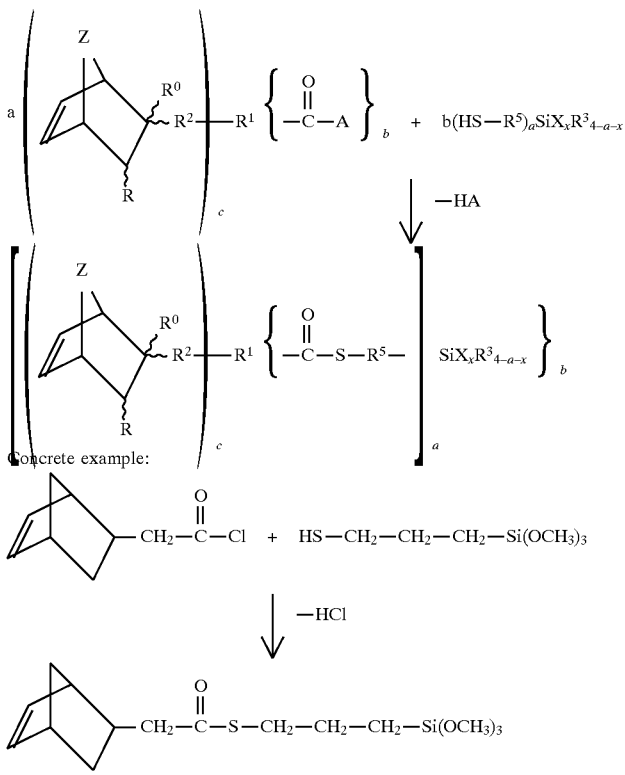

Reaction with silanes with hydroxyl groups:

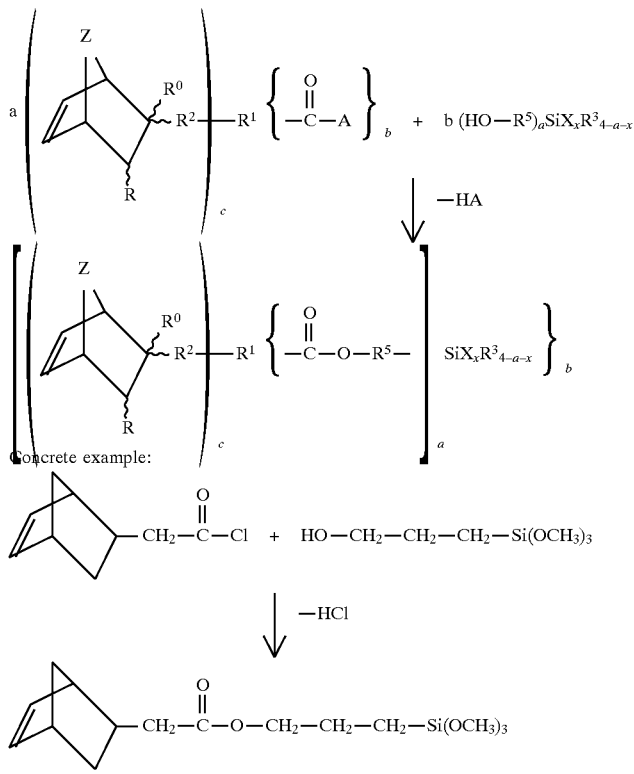

The groups $R^1$ of the bicyclic components can in each case contain up to b carboxylic acid derivatives, so that in each case up to b silane units can be added to the radical $R^1$. The silanes used can in each case have up to a thiol or hydroxyl groups, so that up to a bicyclic groups can be added to a silane. In addition, the radical $R^1$ can contain up to c norbornene or oxabicycloheptene units. Entirely by analogy, norbornenes and oxabicycloheptenes of general formula (XVII) are also reacted.

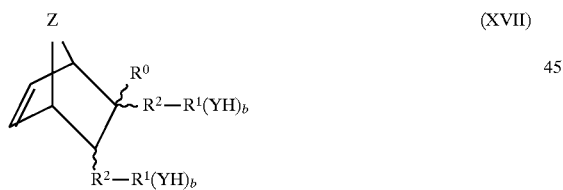

(XVII)

The following additions are also possible, where the groups and indices are as defined for general formula (Ia) and the index a is preferably >1:

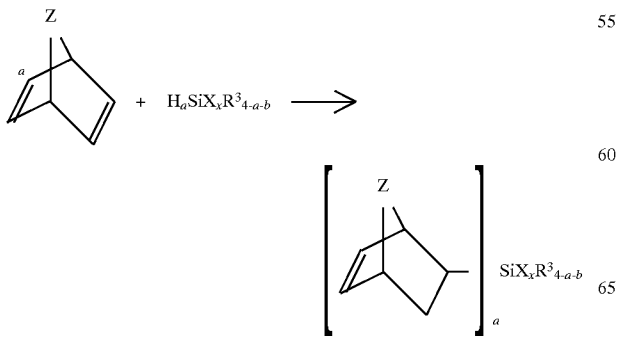

-continued

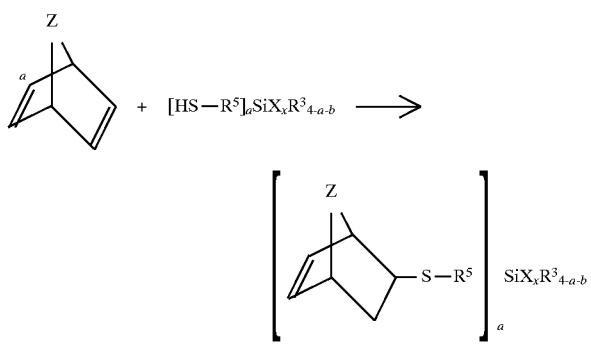

Also, the norbornene unit can be obtained via a Diels-Alder addition of a furan or cyclopentadiene derivative to an organically modified silane whose organic group(s) has/have one or more C=C double bonds. The general reaction schemes are as follows, wherein the groups and indices are as defined for general formula (Ia).

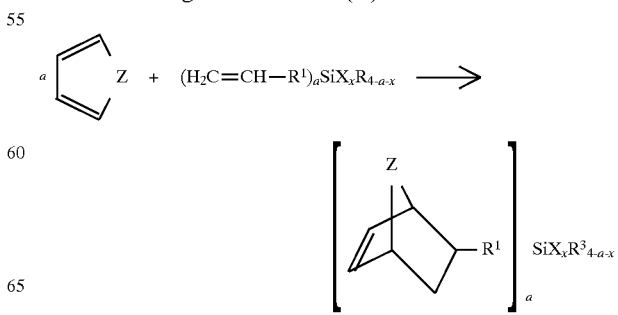

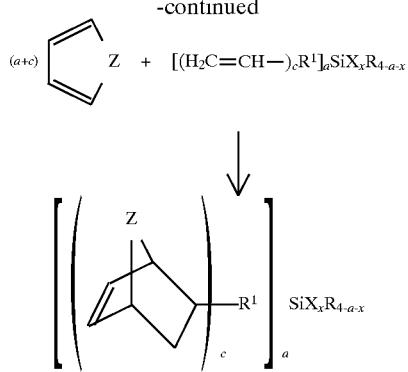

If the radical R¹ contains more than one terminal C=C double bond, then more than one furan or cyclopentadiene unit can be added.

The silanes used in the examples described above can be purchased or prepared according to methods as described e.g. in "Chemie und Technologie der Silicone" (W. Noll, Verlag Chemie GmbH, Weinheim/Bergstrasse, 1968), in DE-C-40 11 044 or in DE 44 16 857.

The norbornene or oxabicycloheptene derivatives used can be obtained e.g. by the usual functionalisation of norbornadiene and oxabicycloheptadiene derivatives or by a Diels-Alder addition of furan or cyclopentadiene derivatives to C=C double bonds. Starting components of formula (XVIII), in which the radicals and indices are as defined for general formula (Ia), can be obtained e.g. according to the following reaction sequence.

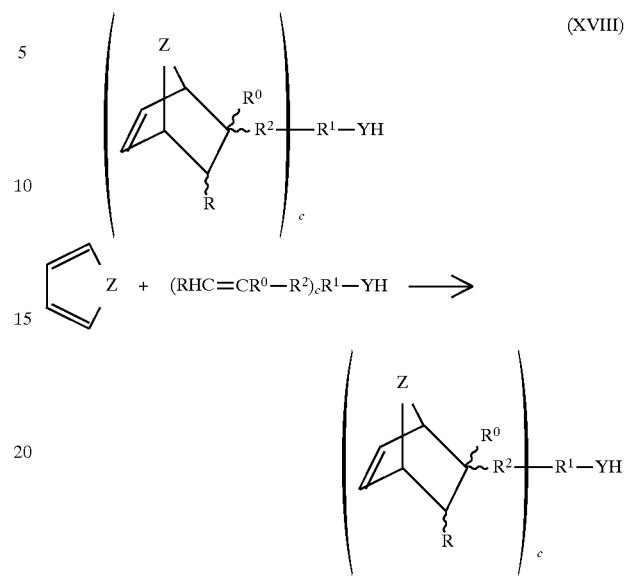

Further concrete examples for preparing norbornene silanes (Ia) with one or more norbornene units, which can be used according to the invention, are given below.

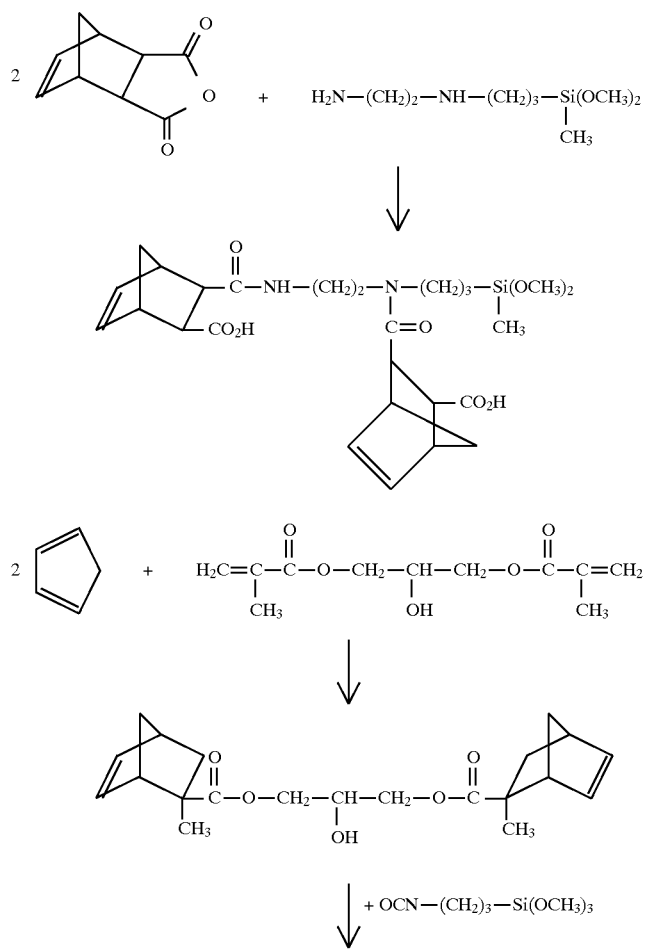

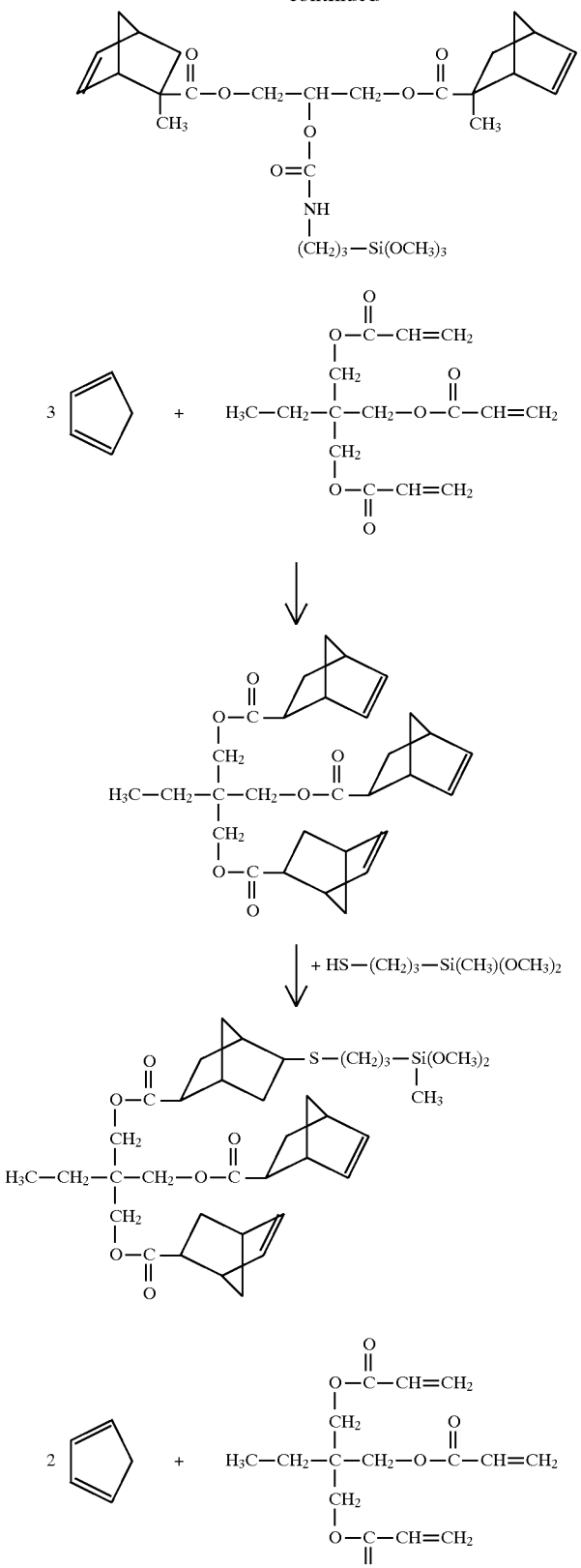

-continued
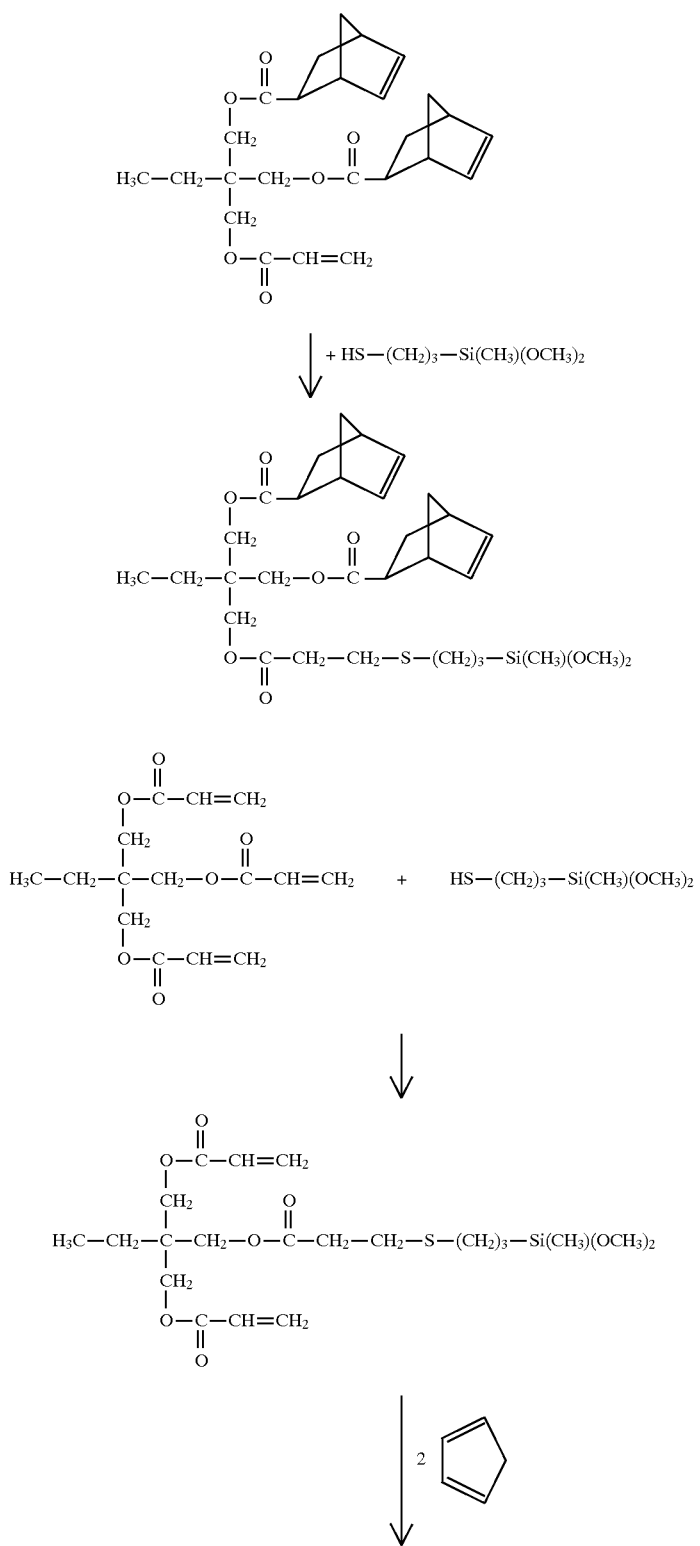

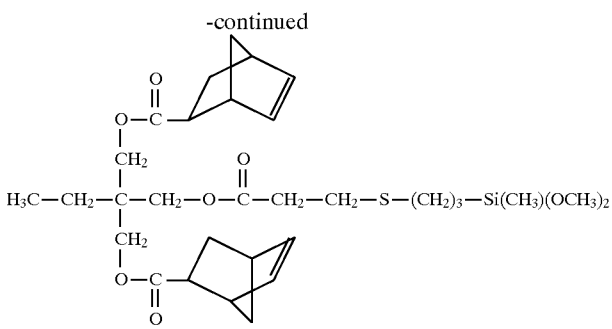

The mercaptosilanes present in the dental material according to the invention are available commercially or can be prepared according to various known methods. One variant is the partial SH-ene addition of multifunctional mercapto compounds to purchasable acryloyl silanes according to the general reaction equation below, wherein the radicals and indices are as defined for formula (Ib).

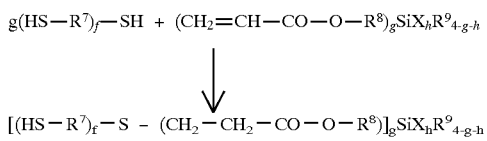

Concrete example:

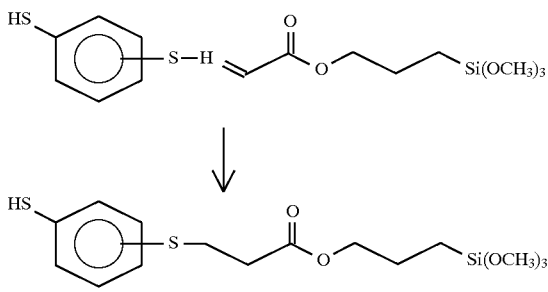

The silicic acid condensates of the norbornene silanes (Ia) and mercaptosilanes (Ib) present in the dental material according to the invention are obtained by hydrolysis of the hydrolysable groups X contained in the silanes (Ia) and (Ib), e.g. alkoxy groups, and subsequent condensation, which leads to the formation of an inorganic network of Si—O—Si units. The hydrolysis and condensation takes place in basic or acidic medium. Preferably, a linking of the C=C double bonds which are contained in the silanes used is avoided. The hydrolysis and condensation preferably takes place in the presence of a condensation catalyst, with compounds providing protons or hydroxyl ions, such as organic or inorganic acids or bases, being preferred. Particularly preferred are volatile acids and bases, in particular hydrochloric acid or ammonia. It has proved successful to adopt methods used in sol-gel technology during the hydrolysis and condensation, as described e.g. in C. J. Brinker et al., "Sol-Gel Science", Academic Press, Boston, 1990. In addition, the "sol-gel process" is described in DE-A-27 58 414, DE-A-27 58 415, DE-A-30 11 761, DE-A-38 26 715 and DE-A-38 5 35 968.

It is particularly preferred that the stoichiometric quantity of water required for complete hydrolysis of all hydrolysable groups is added in the form of water-containing alcohols or moisture-containing adsorbents and the hydrolysis and condensation is carried in a solution of aliphatic alcohols or esters at temperatures in the range from preferably −5° to +30° C.

The silicic acid condensates of the norbornene silane (Ia) and mercaptosilane (Ib) can, however, also be used in the incompletely hydrolysed and condensed form. In such cases, they are referred to as precondensates.

In addition to at least one silicic acid condensate of the norbornene silane (Ia) or at least one silicic acid condensate of the mercaptosilane (Ib), the dental material according to the invention can also contain further hydrolytically condensable compounds, which are used as they are or in the form of precondensates or completely hydrolysed and condensed products.

Preferably, at least one silane of general formula (VIII) is used as further hydrolytically condensable compound $$R^{10}_k(Z'R^{11})_m SiX'_{4-(k+m)} \quad \text{(VIII)}$$

wherein $R^{10}$, $Z'$, $R^{11}$, $X'$, k and m have, unless stated otherwise, independently of one another, the following meanings:

$R^{10}$=$C_1$ to $C_8$ alkyl, $C_1$ to $C_{12}$ alkenyl or $C_6$ to $C_{14}$ aryl, $R^{11}$=$C_1$ to $C_8$ alkylene, $C_1$ to $C_{12}$ alkenylene or $C_6$ to $C_{14}$ arylene, $X'$=H, halogen, OH, $C_1$ to $C_8$ alkoxy, $Z'$=mercapto, carboxy, acrylic, methacrylic, allyl, vinyl or vinylether group;

k=0, 1, 2 or 3, m=0, 1, 2 or 3, and k+m=1, 2 or 3.

Such silanes are for example described in DE-C-34 07 087.

Specific examples of hydrolytically condensable silanes of general formula (VIII) are:

$CH_3$—Si—$Cl_3$, $CH_3$—Si—$(OC_2H_5)_3$, $C_2H_5$—Si—$Cl_3$, $C_2H_5$—Si—$(OC_2H_5)_3$, $CH_2$=CH—Si—$(OCH_2H_5)_3$, $CH_2$=CH—Si—$(OC_2H_4OCH_3)_3$, $(CH_3)_2$—Si—$Cl_2$, $CH_2$=CH—Si—$(OOCCH_3)_3$, $(CH_3)_2$—Si—$(OC_2H_5)_2$, $(C_2H_5)_3$—Si—Cl, $(C_2H_5)_2$—Si—$(OC_2H_5)_2$, $(CH_3)_2(CH_2$=CH)—Si—$Cl_2$, $(CH_3)_3$—Si—Cl, $(t$-$C_4H_9)(CH_3)_2$—Si—Cl, $(CH_3O)_3$—Si—$C_3H_6$—NH—$C_2H_4$—N—$C_2H_4$—$NH_2$, $(CH_3O)_3$—Si—$C_3H_6$—SH, $(CH_3O)_3$—Si—$C_3H_6$—NH—$C_2H_4$—$NH_2$, $(CH_3O)_3Si$—$C_3H_6$—Cl, $(CH_3O)_3$—Si—$C_3H_6$—O—C(O)—C($CH_3$)=$CH_2$, $(CH_3)_2(CH_2$=CH—$CH_2$)—Si—Cl, $(C_2H_5O)_3$—Si—$C_3H_6$—$NH_2$, $(C_2H_5O)_3$—Si—$C_3H_6$—CN,

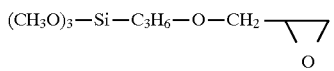

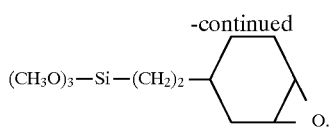

In addition, as preferred further hydrolytically condensable compounds, at least one aluminium, titanium or zirconium compound of formula $$AlR^{12}_3 \text{ or } M X''_y R^{13}_z$$

can also be used, wherein M, $R^{12}$, $R^{13}$, $X''$, y and z have, independently of one another, the following meanings:

M=Ti or Zr,
$R^{12}$=halogen, OH, $C_1$ to $C_8$ alkoxy,
$R^{13}$=R, as defined in claim 1,
$X''$=halogen, OH or $C_1$ to $C_8$ alkoxy,
y=1 to 4, in particular 2 to 4,
z=0 to 3, in particular 0 to 2.

Preferred examples of the aluminium compounds used are $Al(OCH_3)_3$, $Al(OC_2H_5)_3$, $Al(O-n-C_3H_7)_3$, $Al(O-i-C_3H_7)_3$, $Al(OC_4H_9)_3$, $Al(O-i-C_4H_9)_3$, $AlCl_3$ and $AlCl(OH)_2$. Compounds which are liquid at room temperature, such as e.g. aluminium-sec-butylate and aluminium- isopropylate, are particularly preferred.

Preferred examples of the titanium and zirconium compounds which can be used are $TiCl_4$, $Ti(OC_2H_5)_4$, $Ti(OC_3H_7)_4$, $Ti(O-C_4H_9)_4$, $Ti(2\text{-ethylhexoxy})_4$, $ZrCl_4$, $Zr(OC_2H_5)_4$, $Zr(OC_3H_7)_4$, $Zr(OC_4H_9)_4$, $Zr(2\text{-ethyl-hexoxy})_4$ and $ZrOCl_2$.

It is particularly preferred that the silicic acid condensate of the norbornene silane (Ia) or the silicic acid condensate of the mercaptosilane (Ib) used according to the invention and optionally further present hydrolytically condensable compounds are subjected to the hydrolysis and condensation together and thus used as mixed precondensates or mixed condensates.

Obtained silicic acid condensates of the silanes (Ia) and (Ib) used according to the invention and optionally further hydrolysable and condensable compounds can be used either as they are or after partial or almost complete removal of the solvent used. In some cases it can prove advantageous to replace water and optionally used solvent in the product obtained after the polycondensation by another solvent in order to stabilise the silicic acid condensate. For this purpose, the reaction mixture can be thickened, e.g. in a vacuum at slightly raised temperature, until it can still easily be taken up in another solvent.

The silanes (Ia) and (Ib) are stable compounds and they can either be processed on their own or together with other hydrolysable, condensable and/or polymerisable or polyaddable components to give silicic acid polycondensates and silicic acid heteropolycondensates also useful in the dental material according to the invention.

It is preferred that the silicic acid condensate of the norbornene silane (Ia) and the mercaptosilane (Ib) are contained together with a reactant for a thiol-ene polymerisation in the dental material according to the invention.

Preferred reactants for the silicic acid condensate of the norbornene silane (Ia) are the mercaptosilane (Ib), a silicic acid condensate of the mercaptosilane (Ib) and/or an oligo- or poly(thiol) compound. Examples of usable oligo- or poly(thiol) compounds are in particular o-, p- or m-dimercaptobenzene or esters of thioglycollic or 3-mercaptopropionic acid with linear or branched $C_2$ to $C_{18}$ polyols, particularly preferably 1,2-ethane- and 1,6-hexanedithiol, α,ω-triethyleneglycoldithiol, the thioglycollic acid or 3-mercaptopropionic acid esters of ethylene, propylene and butylene glycol and of 1,6-hexanediol, glycerol, trimethylolpropane and pentaerythritol.

On the other hand, preferred reactants for the silicic acid condensate of the mercaptosilane (Ib) are the norbornene silane (Ia), a silicic acid condensate of the norbornene silane (Ia) and/or an oligo- or poly(norbornene) compound. Examples of suitable oligo- or poly(norbornene) compounds are in particular Diels-Alder addition products of cyclopentadiene with di- or multi(meth)acrylates, esters or urethanes of 5-norbornene-2-methanol or 5-norbornene-2-ol with di- or polycarboxylic acids or di- or polyisocyanates, particularly preferably Diels-Alder addition products of cyclopentadiene with polyfunctional (meth)acrylic acid esters of ethylene, propylene and butylene glycol and of 1,6-hexanediol, glycerol, trimethylolpropane and pentaerythritol and the polyfunctional esters of 5-norbornene-2-methanol and malonic, maleic, succinic, glutaric, terephthalic and isophthalic acid.

The thiol-ene polymerisation of the dental material according to the invention leads to the addition of thiol groups of one component to C═C double bonds of the other component, and inorganic-organic composite materials having a high mechanical hardness and strength, which is superior to that of conventional ene-thiol polymerisates, form as reaction products. Also, it is surprising that there is only a very small polymerisation shrinkage during the thiol-ene polymerisation, which is of advantage, particularly when the dental material is used as dental filling material or dental cement.

To initiate the thiol-ene polymerisation, thermal initiators and/or photoinitiators are preferably added to the dental material according to the invention.

Preferred examples of thermal initiators are the known peroxides, such as dibenzoyl peroxide, dilauryl peroxide, tert.-butyl peroctoate or tert.-butyl perbenzoate and azobisisobutyroethyl ester, benzpinacol or 2,2-dimethylbenzpinacol.

Examples of suitable photoinitiators are benzophenone, benzoin and their derivatives or a-diketones and their derivatives, such as 9,10-phenanthrenequinone, diacetyl or 4,4-dichlorobenzil. 2,2-methoxy-2-phenylacetophenone and camphor quinone are preferably used and α-diketones in combination with amines as reducing agents, such as e.g. cyanoethylmethylaniline, methylaminoethyl-methacrylate, triethanolamine, N,N-dimethyl-sym.-xylidine, are particularly preferably used. Further particularly suitable photoinitiators are acyl phosphines, such as e.g. 2,4,6-trimethylbenzoyl-diphenyl- or bis(2,6-dichlorobenzoyl)-4-N-propylphenylphosphinoxide.

For a polymerisation carried out at room temperature, radical chain starters, such as e.g. benzoyl or lauryl peroxide in combination with amines, such as e.g. N,N-dimethyl-sym.-xylidine or N,N-dimethyl-p-toluidine, are used as initiators.

The dental material according to the invention can be used as it is or in at least partially polymerised form.

In addition, the dental material according to the invention can also contain fillers. Examples of preferred fillers are quartz, glass ceramic and glass powders, in particular barium silicate glass powder, lithium/aluminium silicate glass powder and barium glass powder, aluminas or silicas, very finely divided silicas, in particular pyrogenic or precipitated silicas, and X-ray-opaque fillers, such as ytterbium trifluoride.

A particularly preferred dental material according to the invention contains (a) 5 to 80, in particular 10 to 60 wt. %, of silicic acid condensate of the norbornene silane (Ia) or the mercaptosilane (Ib), and (b) 0 to 50, in particular 0 to 30 wt. %, of further hydrolytically condensable compounds, optionally in the form of condensates, (c) 5 to 80, in particular 20–70 wt. %, of reactants for thiol-ene polymerisation, (d) 0.1 to 5, in particular 0.2. to 2 wt. %, of polymerisation initiators, and/or (e) 0 to 90 wt. %, in particular 0 to 80 wt. %, of fillers.

The dental material according to the invention is used in particular by applying it to the area of artificial or natural teeth material to be treated and curing it, in particular using a thiol-ene polymerisation.

The dental material is preferably used as a dental cement, dental filling material or dental bonding for filling materials in a manner conventional for these specific types of dental materials. Thus, the invention provides also for a method of bonding artificial or natural teeth material to a dental material by applying dental cement or bonding according to the invention. Additionally, the invention provides for a method of filling tooth material by applying dental filing material according to the invention.

A particular advantage of the dental material according to the invention has proven to be that on the one hand it shows a small polymerisation shrinkage and on the other hand results in composite materials having high mechanical strength. It is precisely such a combination of properties which is of particular significance for dental materials.

Furthermore, it is also possible to add customary auxiliaries and additives to the dental material, such as e.g. dyes, pigments, thixotropic auxiliaries, stabilisers, plasticisers, perfumes or microbicidal active ingredients.

The invention will in the following be described in more detail with reference to examples.

EXAMPLE 1

3-(bicyclo[2.2.1]hept-2-ene-5-methyl-5-carbonyloxy)propyltrimethoxy silane (1)

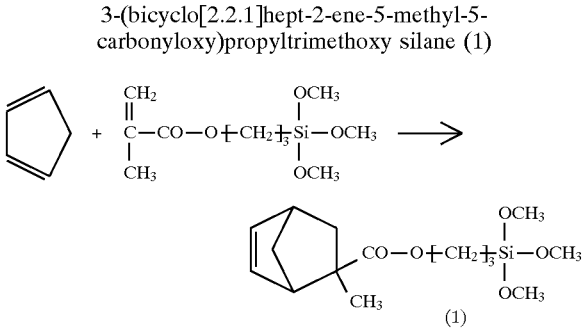

59.1 g (0.20 mol) 3-methacryloyloxypropyltrimethoxy silane and some hydroquinone monomethyl ether (MEHQ) are placed in a sulphonation flask which is connected via a distillation bridge to a cracking apparatus. After flushing with argon, cyclopentadiene is fed into the reaction vessel, with simultaneous stirring and warming to 85 to 90° C. After 33 hours the reaction has finished and formed dicyclopentadiene is distilled off at 0.05 mbar. Following subsequent fractional distillation in a high vacuum, the norbornene silane (1) (bp: 98°–100° C./7.0 mPa) is obtained as a colourless liquid in 70% yield.

Elemental analysis: $C_{15}H_{26}O_5Si$ Calc.: C 57.30 H 8.33 (314.45) Found: C 57.12 H 8.31

$^1$H NMR (CDCl$_3$, 90 MHz): 0.38–0.83 (2H, m, Si—CH$_2$), 1.10–2.57 (9H, m, C—CH$_3$ and 3×—CH$_2$), 2.72–3.17 (2H, m, >CH—), 3.57 (9H, s, O—CH$_3$), 4.07 (2H, t, O—CH$_2$) and 6.00–6.28 (2H, m, =CH—).

IR (film, cm$^{-1}$): 1725 (C=O), 725 (H—C=C).

EXAMPLE 2

3-(bicyclo[2.2.1]hept-2-ene-5-carbonyloxy)propyldimethoxymethylsilane (2)

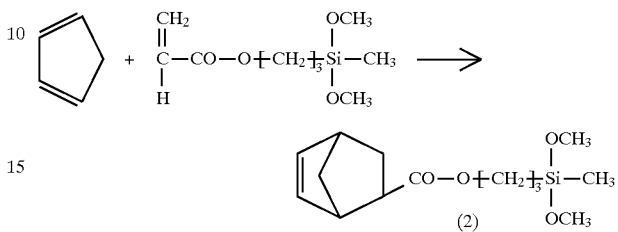

The method is the same as described in Example 1 except 3-acryloyloxypropylmethyldimethoxysilane is used as dienophile. The reaction has finished after just 7 hours. After removing the dicyclopentadiene, fractional distillation in a high vacuum produces the norbornene silane (2) (bp.: 94°–96° C./4.0 mPa) as a colourless liquid in 89% yield.

Elemental analysis: $C_{14}H_{24}O_4Si$ Calc.: C 59.12 H 8.50 (284.42) Found: C 58.58 H 8.23

$^1$H NMR (CDCl$_3$, 90 MHz): 0.13 (3H, s, Si—CH$_3$), 0.55–0.77 (2H, m, Si—CH$_2$), 1.22–2.07 (6.5H, m, —CH$_2$—/>CH—CO$_{exo}$), 2.83–3.30 (2.5H, m, >CH—/>CH—CO$_{endo}$), 3.55 (6H, s, O—CH$_3$), 4.00 (2H, t, O—CH$_2$) and 5.88–6.27 (2H, m, =CH—).

IR (film, cm$^{-1}$): 1732 (C=O), 712 (H—C=C).

EXAMPLE 3

3-(bicyclo[2.2.1]hept-2-ene-5-methoxycarbamoyl)propyltriethoxysilane (3)

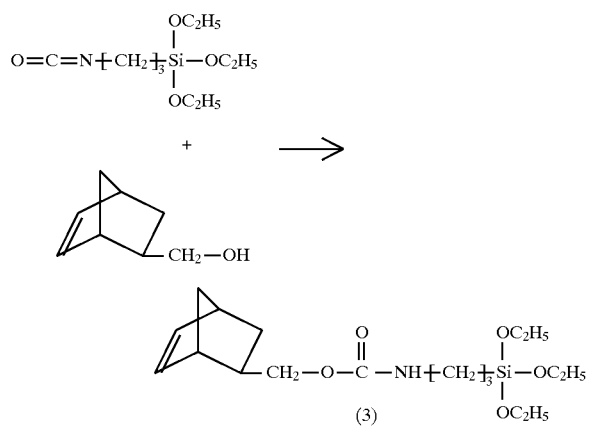

To a mixture of 24.8 g (0.20 mol) 5-norborn-2-ene methanol, 0.1 g di-n-butyl tin carboxylate (Metatin 801) as catalyst and 40 mg hydroquinone monomethyl ether (MEHQ) are added dropwise 49.2 g (0.20 mol) 3-isocyanatopropyltriethoxysilane (IPTES) with stirring and cooling. The mixture is then stirred for 72 hours at room temperature until the isocyanate groups are spent. Fractional distillation produces the silane (3) (bp.: 136°–140° C. at 5.0 mPa) as a colourless liquid in 76% yield.

Elemental analysis: $C_{18}H_{33}O_5Si$ Calc.: C 58.19 H 8.95 (371.55) Found: C 57.28 H 9.00

$^1$H NMR (CDCl$_3$, 90 MHz): 0.33–0.73 (2H, m, Si—CH$_2$) 1.12–1.92(13H, m, 3×—CH$_2$—, 3×—CH$_3$), 2.23–2.37 (1H, m, >C$\underline{H}$—CH$_2$—O), 2.70–2.93 (2H, m, —CH<), 3.17 (2H, q, NH—C$\underline{H}_2$), 3.67–3.97 (8H, m, O—CH$_2$—), 4.90–5.10 (1H, S,—NH—) and 5.85–6.20 (2H, m, =CH—).

IR (film, cm$^{-1}$): 3342 (NH-urethane), 1726 (C=O), 721 (H—C=C).

EXAMPLE 4

Di(norbornene) compound (4)

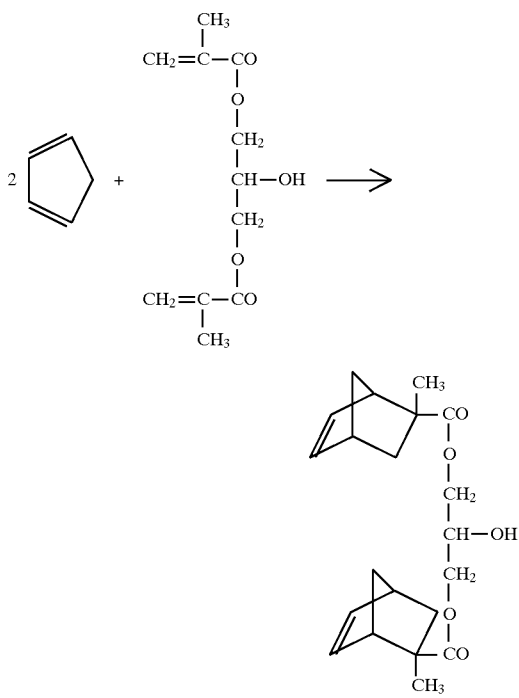

The method is the same as described in Example 1, except 137.0 g (0.6 mol) purchasable glycerin dimethacrylate (R öhm) is used as dienophile. After complete reaction of the methacrylate groups, the volatile constituents are drawn off in a fine vacuum and the desired di(norbornene) compound (4) is obtained, which can be used without purification as reactant for a thiol-ene polymerisation for further reactions.

IR (film, cm$^{-1}$): 3496 (OH, broad), 1730 (C=O), 1572 (C=C, norbornene), 725 (H—C=C)

EXAMPLE 5

Di(norbornene)silane (5)

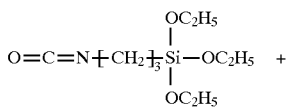

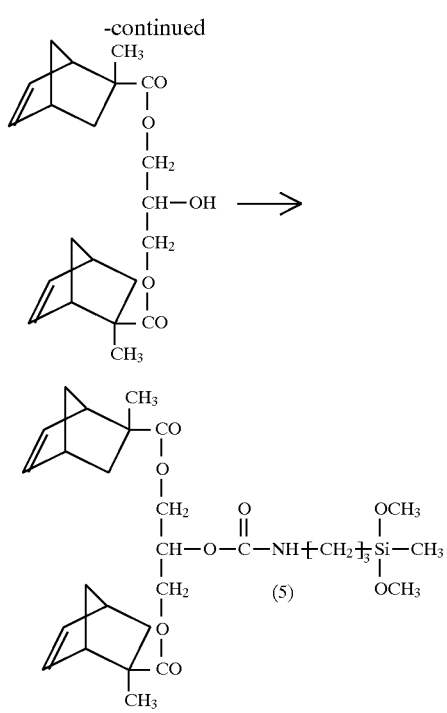

The method is the same as described in Example 3, except that a solution of 14.4 g (40 mmol) of the OH group-containing di(norbornene) compound (4) in approx. 20 ml absolute THF is reacted with 9.9 g (40 mmol) IPTES. The mixture is stirred for 48 hours at room temperature and reduced to constant weight in a fine vacuum, whereupon the di(norbornene) silane (5) is obtained in almost quantitative yield.

IR (film, cm$^{-1}$): 3380 (NH-urethane), 1733 (C=O), 725 (H—C=C)

EXAMPLE 6

Production of a silicic acid condensate based on the norbornene silane (1)

20 mmol norbornene silane (1) and 20 mmol dimethyl dimethoxy silane are dissolved in 50 ml anhydrous ethanol. After adding 50 mmol water as a mixture with 5 ml ethanol and a few drops of 0.1 molar ethanolic acetic acid solution, the mixture is heated under reflux for 5 hours and stirred overnight. After removing the volatile components in vacuum, the formed resinous silicic acid condensate (7 g) can be used for the thiol-ene polymerisation.

EXAMPLE 7

Preparation of a dental bonding

To 7 g silicic acid condensate according to Example 6 are added 21 mg camphor quinone (0.3 wt. %) as initiator and 35 mg (0.5 wt. %) 2-ethyl-hexyl-N,N-dimethyl-4-aminobenzoate. 5.0 mmol pentaerythritol tetra(3-mercaptopropionate) (PETMP) (Evans Chemetics) are then added as reactant for the thiol-ene polymerisation, the mixture is poured out as a film and irradiated for 60 seconds with a dental light source, namely Heliomat (Vivadent). A solid, well adhering film forms. The densities of the resinous silicic acid condensate used and the polymerisate were determined according to the buoyancy method. The change in volume during the thiol-ene polymerisation was determined from the density difference.

The obtained ΔV value of only 0.5% was clearly lower than that for conventional bondings based on methacrylate. For example, the volume shrinkage during the curing of a conventional bonding having the composition below is 7.5%.

Composition of a conventional bonding

| Component | Wt. % |
|---|---|
| Bis-GMA* | 60 |
| Triethyleneglycol dimethacrylate | 39.26 |
| Cyanoethylmethyl aniline | 0.5 |
| Camphor quinone | 0.24 |

Bis-GMA*= 2,2-bis-4-(3-methacryloxy-2-hydroxy-propoxy)-phenylpropane

EXAMPLE 8

Production of a silicic acid condensate from a mixture of the di(norbornene) silane (5) and the di(norbornene) compound (4)

40 mmol di(norbornene) silane (5) are mixed with 16 mmol di(norbornene) compound (4) and 25 ml acetic acid ethyl ester. mixed with the corresponding quantity of water for hydrolysis/condensation of the triethoxysilyl groups (10 mmol $H_2O$ per $OC_2H_5$ group) and worked up in analogous manner to Example 6, whereby a resin having a viscosity of 2800 Pa•s (25°/40° C.) forms in practically quantitative yield. This resin can be used as aconstituent of a dental cement.

EXAMPLE 9
Synthesis of di(norbornene) compound (6)

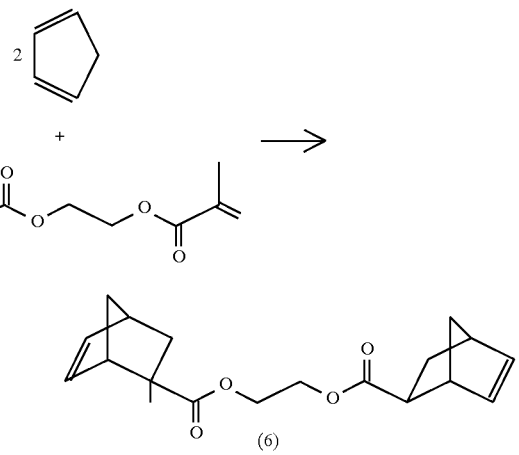

The method is the same as described in Example 1, except that 118.9 g (0.6 Mol) purchasable ethylene glycol dimethacrylate (Fluka) is used as dienophile. After complete reaction of the methacrylate groups, the volatile constituents are removed in a fine vacuum and the desired di(norbornene) compound (6) is obtained, which has a viscosity of approx. 200 mPa•s (25° C.). The HPLC diagram shows that the product contains at least 5 different components, probably configuration isomers. Cyclopentadiene, dicyclo-pentadiene or ethylene glycol dimethacrylate are however no longer detectable. The di(norbornene) compound (6) can be used as a reactive diluentfor a dental cement and as a reactant for a thiol-ene polymerisation. For example, the viscosity of the resin in Example 8 is reduced to 8 Pa•s by diluting with the same amount by weight of di(norbornene) compound (6).

IR data of (6):
IR (film, $cm^{-1}$): 1730 (C=O), 1572 (C=C, norbornene), 724 (H—C=C)

EXAMPLE 10
Synthesis and hydrolysis/condensation of the norbornene silane (7)

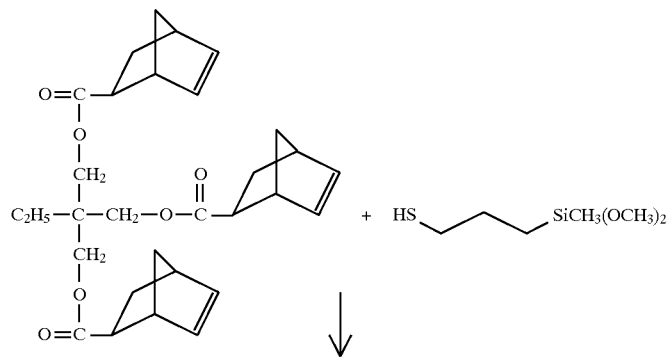

-continued

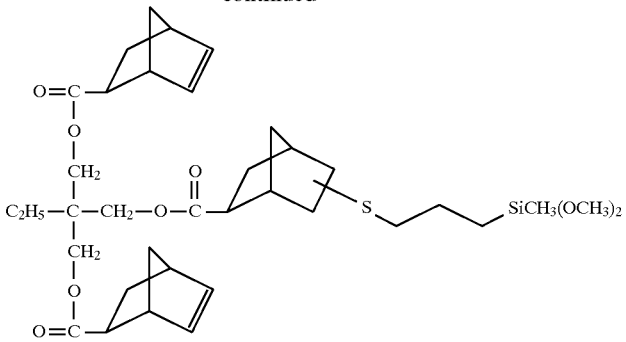

42.7 g (90 mmol) of the Diels-Alder adduct of 1 mol trimethylolpropanetriacrylate with 3 mol cyclopentadiene are dissolved in 90 ml ethyl acetate. 16.2 g (90 mmol) mercaptopropyl-methyldimethoxysilane) are added drop-wise under a protective gas. After thiol addition has taken place (checked using the iodine test), the product solution can be hydrolysed. For this, 5.8 g (18 mmol) dinorbornene compound (4) is added to the product solution as reactive diluent and 2.6 g water as 0.1 n HCl and the mixture is stirred at room temperature. After complete reaction, the mixture is shaken out with water, filtered and volatile components are stripped off in a rotary evaporator at 40° C. After the residual volatile constituents have been removed using an oil pump vacuum at 40° C., a viscous resin is obtained (approx. 820 Pa•s at 25° C.).

EXAMPLE 11

Preparation of a dental cement

A dental cement is prepared from the following components in a rotary mixer:

| Components | Content (Wt. %) |
|---|---|
| Resin from Example 8 | 11.7 |
| Reactive diluent from Example 9 | 11.7 |
| PETMP (Evans Chemetics) | 16.3 |
| Silanised pyrogenic silica Ox-50 (Degussa) | 41.3 |
| Ytterbium fluoride (Rhone-Poulenc) | 18.7 |
| Camphor quinone | 0.2 |
| Eusolex 6007 (2-ethylhexyl-dimethylamino-benzoate) (Merck) as activator | 0.1 |

Test-pieces were prepared from the cement which were then exposed to light using a dental light source, Spectramat (Vivadent) for 10 minutes. For samples which had been stored for 24 hours, the flexural strength was determined as 89 MPa and the E-modulus as 5.5 GPa in accordance with ISO 4049. The polymerisation shrinkage was only 0.9 vol. %.

We claim:

1. A dental material which comprises:

(a) at least one silicic acid condensate of a hydrolysable and polymerisable norbornene silane of general formula (Ia)

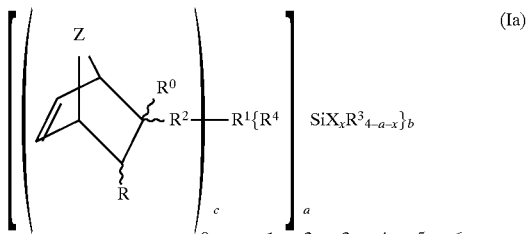

wherein the variables $R^0$, R, $R^1$, $R^2$, $R^3$, $R^4$, $R^5$, $R^6$, X, Y, Z, a, b, c, x have, independently of one another, the following meanings:

$R^0 = C_1$ to $C_8$ alkyl or H;

R = $C_1$ to $C_8$ alkyl or alkenyl or $C_6$ to $C_{10}$ aryl, where these radicals can be interrupted by O or S atoms or by —O—CO—, —CO—O— or NH groups or can contain these atoms or groups in terminal position, or H or $R^2$—$R^1$—$R^4$—$SiX_xR^3{}_{3-x}$;

$R^1$ = missing or $C_1$ to $C_8$ alkylene or $C_6$ to $C_{14}$ arylene, arylenalkylene or alkylenarylene, where these radicals can be interrupted by O or S atoms or by —O—CO—, —CO—O— or NH groups or can contain these atoms or groups in terminal position;

$R^2$ = missing or $C_1$ to $C_8$ alkylene or $C_6$ to $C_{14}$ arylene, arylenalkylene or alkylenarylene, where these radicals can be interrupted by O or S atoms or by —O—CO—, —CO—O— or NH groups or can contain these atoms or groups in terminal position;

$R^3 = C_1$ to $C_{10}$ alkyl or alkenyl or $C_6$ to $C_{10}$ aryl, where these radicals can be interrupted by O or S atoms or can contain these atoms in terminal position;

$R^4$ = —$(CHR^6-CHR^6)_n$—, with n=0 or 1, —$CHR^6$—$CHR_6$—S—$R^5$—, —CO—S—$R^5$—, —$CHR^6$—$CHR^6$—$NR^6$—$R^5$—, —S—$R^5$, —Y—CO—NH—$R^5$— or —CO—O—$R^5$—;

$R^5 = C_1$ to $C_8$ alkylene or $C_6$ to $C_{10}$ arylene, where these radicals can be interrupted by O or S atoms or by —O—CO—, —CO—O— or NH groups or can contain these atoms or groups in terminal position;

$R^6$ = H, $C_1$ to $C_{10}$ alkyl or $C_6$ to $C_{10}$ aryl;

X = a hydrolysable group, in particular halogen, OH or alkoxy;

Y = O, S or $NR^6$;

Z = O or $CHR^6$;

a = 1, 2 or 3;

b = 1, 2 or 3;

c = 1 to G; and x = 1, 2 or 3;

wherein a and/or b=1 and a+x=2, 3 or 4.

or (b) at least one silicic acid condensate of a hydrolysable and polymerisable mercaptosilane of general formula (Ib)

           (Ib)

wherein the variables $R^7$, $R^8$, $R^9$, X, f, g and h have, independently of one another, the following meanings:
$R^7$=$C_1$ to $C_{10}$ alkylene or alkenylene or $C_6$ to $C_{14}$ arylene or alkylarylene, where these radicals can be interrupted by O or S atoms or by —CO—O— or —O—CO— groups or can contain these atoms or groups in terminal position; $R^8$=$C_1$ to $C_{10}$ alkylene or alkenylene or $C_6$ to $C_{14}$ arylene or alkylarylene, where these radicals can be interrupted by o or S atoms or —CO—O— or —O—CO— groups or can contain these atoms or groups in terminal position;
$R^9$=$C_1$-$C_{10}$ alkyl or alkenyl or $C_6$-$C_{14}$ aryl or alkylaryl, where these radicals can be interrupted by O or S atoms or —CO—O— or —O—CO— groups or can contain these atoms or groups in terminal position;
X=a hydrolysable group, in particular halogen, hydroxy or alkoxy;
g=1, 2 or 3;
f=1, 2, 3 or 4; and
h=1, 2 or 3.

2. The dental material according to claim 1, wherein at least one of the variables of formula (Ia) has, independently of the other variables, the following meaning:
$R^0$=$C_1$ to $C_5$ alkyl or H;
R=H or $C_1$ to $C_5$ alkyl;
R=$C_1$ to $C_8$ alkylene, where these radicals can be interrupted by O or S atoms or by —O—CO— or —CO—O— groups or can contain these atoms or groups in terminal position;
$R^2$=$C_1$ to $C_8$ alkylene, where these radicals can be interrupted by O or S atoms or can contain these atoms in terminal position;
$R^3$=$CH_3$, $C_2H_5$ or phenyl;
$R^4$=—($CHR^6$—$CHR^6$)$_n$—, —S—$R^5$—, —Y—CO—NH—$R^5$—, or —CO—O—$R^5$—;
$R^5$=$C_1$ to $C_8$ alkylene, where these radicals can be interrupted by O or S atoms or by —O—CO— or —CO—O— groups or can contain these atoms or groups in terminal position;
$R^6$=H or C, to $C_5$ alkyl;
X=$OCH_3$ or $OC_2H_5$;
Y=O or S;
Z=$CH_2$;
a=1;
b=1;
c=1 or 2;
x=2 or 3; and/or
a+x=3 or 4.

and at least one of the variables of formula (Ib) has, independently of the other variables, the following meaning:
$R^7$=$C_1$ to $C_{10}$ alkylene or $C_6$ to $C_{14}$ arylene, where these radicals can be interrupted by O or S atoms or by —CO—O— or —O—CO— groups or can contain these atoms or groups in terminal position;
$R^8$=$C_1$ to $C_{10}$ alkylene or $C_6$ to $C_{14}$ arylene, where these radicals can be interrupted by O or S atoms or by —CO—O— or —O—CO— groups or can contain these atoms or groups in terminal position;

$R^9$=$C_1$ to $C_{10}$ alkyl; and/or
h=2 or 3.

3. The dental material according to claim 1, wherein
a=1 and b=1
so that the norbornene silane corresponds to the general formula (IIa)

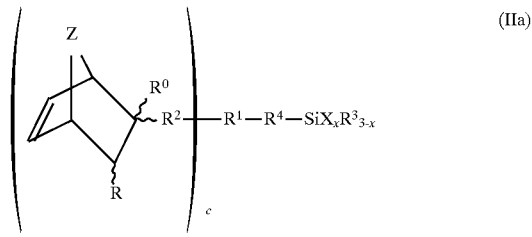           (IIa)

or
g=1
so that the mercaptosilane corresponds to the general formula (IIb):

           (IIb)

4. The dental material according to claim 1, wherein
a=1 and c=1
so that the norbornene silane corresponds to the general formula (IIIa):

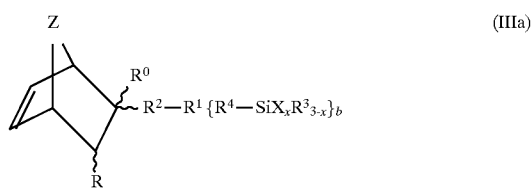           (IIIa)

or
f=1 and g=1
so that the mercaptosilane corresponds to the general formula (IIIb):

           (IIIb)

5. The dental material according to claim 1, wherein
b=1 and c=1
so that the norbornene silane corresponds to the general formula (IVa):

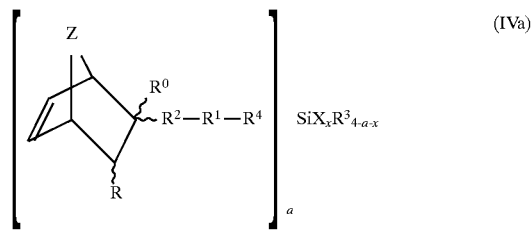           (IVa)

or
f=1
so that the mercaptosilane corresponds to the general formula (IVb):

           (IVb)

6. The dental material according to claim 1, wherein
a=1 and b=1 and c=1
so that the norbornene silane corresponds to general formula (Va):

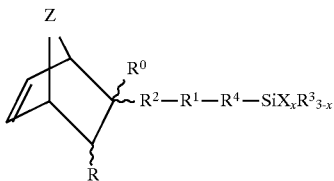

(Va)

7. The dental material according to claim 1 which further comprises hydrolytically condensable compounds.

8. The dental material according to claim 7 which comprises at least one silane of general formula (VIII) as the hydrolytically condensable compounds

(VIII)

wherein $R^{10}$, $Z'$, $R^{11}$, $X'$, k and m have, independently of one another, the following meanings:
$R^{10}$=$C_1$ to $C_8$ alkyl, $C_1$ to $C_{12}$ alkenyl or $C_6$ to $C_{14}$ aryl,
$R^{11}$=$C_1$ to $C_8$ alkylene, $C_1$ to $C_{12}$ alkenylene or $C_6$ to $C_{14}$ arylene,
$X'$=H, halogen, OH, $C_1$ to $C_8$ alkoxy,
$Z'$=mercapto, carboxy, acrylic, methacrylic, allyl, vinyl or vinylether group;
k=0, 1, 2 or 3,
m=0, 1, 2 or 3, and
k+m=1, 2 or 3.

9. The dental material according to claim 7, which comprises, as the hydrolytically condensable compounds, at least one aluminium, titanium or zirconium compound of formula

wherein M, $R^{12}$, $R^{13}$, X", y and z have, independently of one another, the following meanings:
M=Ti or Zr,
$R^{12}$=halogen, OH, $C_1$ to $C_8$ alkoxy,
$R^{13}$=R, as defined in claim 1,
X"=halogen, OH or $C_1$ to $C_8$ alkoxy,
y=1 to 4, and
z=0 to 3.

10. The dental material according to claim 1, which further comprises at least one reactant for a thiol-ene polymerisation.

11. The dental material according to claim 10, wherein the at least one reactant comprises
  (a) the mercaptosilane of general formula (Ib), a silicic acid condensate of the mercaptosilane of general formula (Ib) or an oligo- or poly(thiol) compound as the reactant for the silicic acid condensate of the norbornene silane, or
  (b) the norbornene silane of general formula (Ia), a silicic acid condensate of the norbornene silane of general formula (Ia) or an oligo- or poly(norbornene) compound as the reactant for the silicic acid condensate of the mercaptosilane.

12. The dental material according to claim 11, which comprises
  (a) o-, p- or m-dimercaptobenzene or esters of thioglycollic- or 3-mercaptopropionic acid with linear or branched $C_2$ to $C_{18}$ polyols as said oligo- or poly(thiol) compound, and
  (b) Diels-Alder addition products of cyclopentadiene with di- or multi(meth)acrylates, esters or urethanes of 5-norbornene-2-methanol or 5-norbornene-2-ol with di- or polycarboxylic acids or di- or polyisocyanates as said oligo- or poly(norbornene) compound.

13. The dental material according to claim 10, which further comprises a polymerisation initiator.

14. The dental material according to claim 1 wherein the dental material is at least partially polymerised.

15. The dental material according to claim 13, which comprises:
  (a) 5 to 80 wt. % silicic acid condensate of the mercaptosilane or silicic acid condensate of the norbornene silane,
  (b) 0 to 50 wt. % further hydrolytically condensable compounds, optionally in the form of their silicic acid condensates,
  (c) 5 to 80 wt. % reactants for a thiol-ene polymerisation,
  (d) 0.1 to 5 wt. % polymerisation initiator, and
  (e) 0 to 90 wt. % fillers.

16. A method of applying a dental material comprisinq:
applying said dental material according to claim 1 to a teeth material to be treated and subjecting the dental material to a thiol-ene polymerisation.

17. The dental material according to claim 9, wherein y is 2 to 4 and z is 0 to 2.

18. The dental material according to claim 13, wherein the polymerisation initiator is for a thiol-ene polymerisation.

19. The dental material according to claim 15, which comprises:
  (a) 10 to 60 wt. % silicic acid condensate of the mercaptosilane or silicic acid condensate of the norbornene silane,
  (b) 0–30 wt. % further hydrolytically condensable compounds,
  (c) 20–70 wt. % reactants for a thiol-ene polymerisation,
  (d) 0.2 to 2 wt. % polymerisation initiator; and
  (e) 0 to 80 wt. % fillers.

20. The method according to claim 16, wherein said dental material is selected from the group consisting of a dental cement, a dental filling material, and a bonding for a dental filling material.

* * * * *